United States Patent [19]

Hölderich et al.

[11] Patent Number: 5,780,686
[45] Date of Patent: Jul. 14, 1998

[54] PROCESS FOR PREPARING 4-OXA-AMINES

[75] Inventors: Wolfgang Hölderich, Frankenthal; Marcus Paczkowski, Darmstadt; Dieter Heinz, Meerbusch, all of Germany

[73] Assignee: Hoechst Aktiengesellschaft, Germany

[21] Appl. No.: 863,259

[22] Filed: May 27, 1997

[30] Foreign Application Priority Data

May 30, 1996 [DE] Germany .................. 196 21 704.0

[51] Int. Cl.$^6$ .................................................. C07C 209/00
[52] U.S. Cl. .................................................. 564/413; 564/447
[58] Field of Search .................................. 564/447, 413

Primary Examiner—Brian M. Burn
Attorney, Agent, or Firm—Bierman, Muserlian and Lucas

[57] ABSTRACT

A process for preparing 4-oxa-amines comprising reacting 1,3-dioxanes with ammonia and hydrogen in the presence of hydrogenation catalysts.

21 Claims, No Drawings

PROCESS FOR PREPARING 4-OXA-AMINES

FIELD OF THE INVENTION

A new process for preparing 4-oxa-amines starting with compounds which are readily available, 1,3-dioxanes, and reacting the same with ammonia and hydrogen in the presence of hydrogenation catalysts (reductive amination).

STATE OF THE ART 4-oxa-amines are industrially valuable intermediates for the synthesis of agrochemicals, pharmaceuticals, solvents and raw materials for the laundry detergent industry. The amines can be prepared from the corresponding 4-oxa-alcohols by nucleophilic substitution or by reductive amination of 4-oxa-aldehydes. Both processes are two-stage processes in the course of which the alcohol or the aldehyde has to be prepared first. In a second reaction stage, the alcohol or aldehyde is then converted into the amino compound. Such a procedure is technically complicated and therefore does not always meet the economic demands made of industrial processes.

OBJECTS OF THE INVENTION

It is an object of the invention to provide a process which avoids the disadvantages indicated, is technically simple to carry out and can be used generally.

It is another object of the invention to provide a selective process able to ensure high yields of the target products.

These and other objects and advantages of the invention will become obvious from the following detailed description.

THE INVENTION

The invention provides a process for preparing 4-oxa-amines of the formula

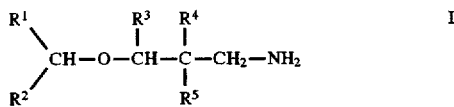

wherein $R^1, R^2, R^4$ and $R^5$ are individually selected from the group consisting of a) hydrogen, b) alkyl, alkenyl and alkynyl of up to 18 carbon atoms, c) cyclalkyl and cycloalkenyl of 5 to 8 carbon atoms, d) aryl, alkylaryl, aralkyl, aralkenyl and alkenylaryl of 6 to 16 carbon atoms and e) heterocyclics, or $R^1$ and $R^2$ and/or $R^4$ and $R^5$ together with the carbon atoms to which they are bound can form a cycloalkane, cycloalkene or a heterocycle, $R^1, R^2, R^4$ and $R^5$ optionally have substituents which are inert under the reaction conditions, and $R^3$ is hydrogen or alkyl comprising reacting 1,3-dioxanes of the formula

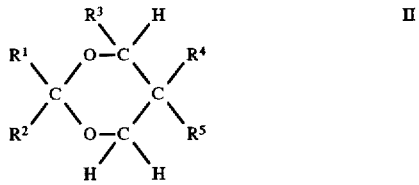

wherein $R^1, R^2, R^3, R^4$ and $R^5$ are as defined above, with hydrogen and ammonia at pressures of 0.1 to 35 MPa and temperatures of 40° to 500° C. in the presence of a hydrogenation catalyst.

Reductive amination is a known reaction for preparing amines which is widely practiced in the industry. Starting materials for this process are exclusively aldehydes and ketones. The reaction of the carbonyl compounds with hydrogen and ammonia is carried out in the presence of hydrogenation catalysts, preferably supported nickel catalysts. The conversion of other compounds according to the principle of reductive amination, particularly the reaction of dioxanes, has not been described hitherto.

Although 1,3-dioxanes can be formally regarded as acetals or ketals, i.e. as reaction products of aldehydes or ketones with 1,3-diols, it was not obvious to use this class of compounds as starting materials for the preparation of amines. In this context, it needs to be taken into account that in synthetic organic chemistry, carbonyl groups are protected by reaction with alcohols, i.e. by acetal or ketal formation, to prevent them from undergoing further reactions. Furthermore, 1,3-dioxanes are compounds having a six-membered ring which, like other six-membered rings, have increased stability for steric reasons. Surprisingly, despite these circumstances which stand in the way of a reaction, it is possible to convert dioxanes into the desired 4-oxa-amines. The high selectivity of the reaction should be particularly emphasized, since a cleavage of the molecule in a way other than to form a 4-oxa compound, for example with formation of smaller fragments, cannot be ruled out.

Preferred 1,3-dioxanes of formula II are compounds in which $R^1, R^2, R^4$ and $R^5$ are individually selected from the group consisting of hydrogen, straight-chain or branched alkyl of 1 to 12 and preferably 1 to 6 carbon atoms, alkenyl and alkynyl of 2 to 12 and preferably 2 to 6 carbon atoms. Preference is also given to compounds of formula II in which $R^1, R^2, R^4$ and $R^5$ are cycloalkyl or cycloalkenyl of 5 or 6 carbon atoms, aryl, alkylaryl, aralkyl, aralkenyl and alkenylaryl of 6 to 12 carbon atoms and heterocyclic radicals containing at least one of the groups consisting of nitrogen, oxygen and/or sulfur. Furthermore, preference is given to 1,3-dioxanes of formula II in which $R^3$ is a straight-chain or branched alkyl of 1 to 12, preferably 1 to 8, and more preferably 1 to 4, carbon atoms. $R^3$ is preferably hydrogen.

Examples of alkyl, alkenyl or alkynyl are methyl, ethyl, n-propyl, i-propyl, propenyl, i-propenyl, n-butyl, i-butyl, n-butenyl, i-butenyl, n-butynyl, pentyl, pentenyl, pentynyl, hexyl, hexenyl, heptyl, heptenyl, octyl, octenyl, nonyl, nonenyl, decyl, decenyl, dodecyl and dodecenyl.

Examples of cycloalkyl are cyclopentyl, cyclohexyl, cycloheptyl, cyclopentenyl and cyclohexenyl.

Examples of aromatics are phenyl, benzyl, 2-phenethyl, 2-phenylpropyl, 3-phenylpropyl, 2-phenylbutyl, 3-phenylbutyl and 4-phenylbutyl.

Examples of heterocyclics are furan, dihydrofuran, tetrahydrofuran, thiophene, dihydrothiophene, pyridine and thiopyran.

The alkyl, cycloalkyl, aromatic and heterocyclic groups may be substituted, particularly by those which are inert under the reaction conditions such as halogen, alkoxy, carboxy or carboxylate. However, in individual cases, it is not ruled out that substituents which react to give certain end products are deliberately selected.

The 1,3-dioxanes used as starting material in the process of the invention are obtainable in various ways. A proven process is the acid-catalyzed addition of 1,3-diols onto aldehydes or ketones or the transacetalation of acetals or ketals, particularly those derived from low-boiling alcohols with 1,3-diols in the presence of acids.

Examples of suitable diol components are 1,3-propanediol, 2-methylpropane-1,3-diol, 2-ethylpropane-1,3-diol, 2-phenylpropane-1,3-diol, 2,2-dimethylpropane-1,3-diol (neopentyl glycol), 2,2-diethylpropane-1,3-diol, 2-methyl-2-ethylpropane-1,3-diol, 2-methyl-2- propylpropane-1,3-diol, 2-methyl-2-butylpropane-1,3-diol, 2-methyl-2-phenylpropane-1,3-diol, 2-ethyl-2-butylpropane-1,3-diol, 1,1-dimethylolcyclohexane, 1,1-dimethylolcyclopentane, 3,3-dimethyloltetrahydrofuran, 3,3-dimethyloltetrahydropyran and 2,2,4-trimethylpentane-1,3-diol.

The carbonyl compound reacted with the 1,3-diols are, for example, aliphatic, aromatic or heterocyclic aldehydes and ketones or their acetals or ketals. Both the aldehydes and ketones can be saturated or unsaturated.

Examples of suitable aliphatic aldehydes are formaldehyde, acetaldehyde, propionaldehyde, butyraldehyde, isobutyraldehyde, n-pentanal, 2-methylbutanal, 3-methylbutanal, n-hexanal, 2-methylpentanal, 3,3-dimethylbutanal, 2-ethylhexanal, 2-methyldecanal, also dialdehydes such as glyoxal, methylglyoxal, malonic dialdehyde, succinic dialdehyde and glutaric dialdehyde, as well as substituted aldehydes such as 3-hydroxy-2,2-dimethylpropanol (hydroxypivalaldehyde), methoxypivalaldehyde, butoxypivalaldehyde, 4-acetoxybutyraldehyde and 5-formylvaleraldehyde.

Unsaturated aliphatic aldehydes also can be used as reaction components for the 1,3-diols, for example acrolein, α-methylacrolein, α-ethylacrolein and higher α-alkylacroleins, isoakylacroleins and alkenylacroleins such as but-2-enal, but-3-enal, 2-methylbut-2-enal, 2-methylpent-2-enal, 2-ethylhex-2-enal, 2,2-dimethylpent-4-enal, 2-methyl-4-acetoxybut-2-enal, 2-methoxymethylacrolein, 2-(3-methoxycarbonylpropyl)acrolein and 2-methyl-4-chlorobut-2-enal.

Examples of aromatic aldehydes are benzaldehyde, p-methoxybenzaldehyde, phenylacetaldehyde, 2-phenylpropanal, 3-phenylpropanal, 2-hydroxybenzaldehyde, 3-hydroxy-4-methoxybenzaldehyde, cinnamaldehyde and benzylacrolein.

Examples of heterocyclic aldehydes are tetrahydrofuryl-2-aldehyde, tetrahydrofuryl-3-aldehyde, tetrahydrothienyl-2-aldehyde, tetrahydrothienyl-3-aldehyde, 5,6-dihydropyranyl-6-aldehyde, 2,5-dimethyl-5,6-dihydropyranyl-6-aldehyde, furyl-2-aldehyde, furyl-3-aldehyde, thienyl-3-aldehyde and 2-, 3- or 4-pyridylaldehyde.

Examples of ketones suitable for preparing the 1,3-dioxanes are acetone, methyl ethyl ketone, diethyl ketone, methyl isopropyl ketone, diisopropyl ketone, diisobutyl ketone, methyl isobutyl ketone, methoxyacetone, methyl phenyl ketone, methyl isopropenyl ketone, methyl isobutenyl ketone, cyclopentanone, cyclohexanone, dimethylcyclopentanone, dimethylcyclohexanone, cyclohexenone, 3,5,5-trimethylcyclohexen-2-one, methyl phenyl ketone, ethyl phenyl ketone and vinyl phenyl ketone, methyl furyl ketone, acetylacetone and acetoacetic esters.

The diols, aldehydes and ketones listed above as building blocks for the 1,3-dioxanes of the present invention are intended only to roughly indicate the range of application of the novel process, but not to restrict it to these compounds mentioned by way of example.

Other reactions which lead to 1,3-dioxanes are the reaction of Grignard reagents with ortho esters and the reaction of alkoxides of diols either with geminal halides or with α-haloethers. Finally, 1,3-dioxanes are also obtainable via the Prins reaction, i.e. the addition of an olefin onto formaldehyde in the presence of an acid.

The reductive amination of the 1,3-dioxanes by the process of the present invention is carried out at 40° to 500° C. Preference is given to temperatures of 100° to 450° C. and more preferably 150° to 350° C. The reaction pressure can be set over a wide range and is from 0.1 to 35 Mpa, with pressures of from 3 to 15 MPa being preferred.

The molar ratio of ammonia to the 1,3-dioxanes is 0.2:1 to 100:1. Ratios of 0.5:1 to 50:1 are preferred. Hydrogen and 1,3-dioxanes are used in molar ratios of 0.2:1 to 250:1 and preferably in ratios of 1:1 to 100:1.

The reactants are reacted in the presence of hydrogenation catalysts which comprise, as hydrogenation-active components, one or more metals of groups VIB, VIIIB, IB and IIB of the Periodic Table of the Elements (designation of groups as used by Chemical Abstracts, which will also be used below). Preferred hydrogenation-active components are molybdenum, tungsten, ruthenium, cobalt, rhodium, iridium, nickel, palladium, platinum and copper. Although these metals can also be employed as catalysts in pure form, e.g. as Raney cobalt or Raney nickel, they are preferably used in the form of supported catalysts.

Suitable supports for the hydrogenation-active metals are acid compounds or mixtures of acid compounds. Among the large number of such substances, zeolites are particularly suitable. This term refers to crystalline, hydrated aluminosilicates having a framework structure and containing alkali metal and/or alkaline earth metal cations. They occur naturally and are also produced synthetically. Zeolites have a structure comprising a regular system of intercrystalline voids which is accessible, via pore openings, to molecules having a similar size.

The framework of zeolites is made up of tetrahedra, with the central atom, which can be either an $Si^{4+}$ or $Al^{3+}$ cation, being surrounded by four oxygen atoms. Each aluminum atom built into the structure leads to a negative charge on the framework, which is balanced by cations such as alkali metal or alkaline earth metal ions. Exchange of the cations is possible since zeolites are inorganic ion exchangers. Thus, for example, alkali metal ions can be replaced by hydrogen ions. In this way, the catalytic activity of the zeolites, which is dependent on the presence of acid centers in the intercrystalline surface, can be varied. The places between the tetrahedra are occupied by water molecules and dehydration by drying or calcination is possible.

In the crystal lattice of synthetically produced zeolites, aluminum can be replaced isomorphiclly by other elements such as boron, gallium, iron, chromium, vanadium, arsenic and antimony. Silicon can be replaced isomorphically by tetravalent elements such as germanium, titanium, zirconium and hafnium. The manner and extent of the replacement of aluminum and/or silicon allow the catalytic properties of the zeolites to be influenced in a targeted manner to be matched to individual requirements.

Zeolites are classified into various groups on the basis of their structure. In the zeolites of the mordenite group, the basic units of the structure, viz. the $SiO_4$ and $AlO_4$ tetrahedra, form chains. The zeolites of the chabasite group are built up of layers of tetrahedra. In the zeolites of the faujasite group, the tetrahedra are arranged to form polyhedra, for example in the form of a cuboctahedron. Depending on the linkage of the cuboctahedra, voids and pores of different sizes are formed and differentiation is accordingly made between, for example, zeolites of the type A, L, X or Y.

Suitable support components for the catalysts used in the process of the invention are zeolites from the faujasite group, e.g. zeolite Y, zeolites from the mordenite group or narrow-pored zeolites, for example of the erionite or chabasite type. Preference is given to using zeolites of the pentasil type which have as basic building block a five-membered ring built up of $SiO_4$ tetrahedra and have a high $SiO_2/Al_2O_3$ ratio. Their pore sizes are between those of the zeolites of type A (pore openings 4.1 Å) and those of X or Y (pore openings 7.4 Å). The pentasil zeolites can have different chemical compositions. Differentiation is accordingly made between aluminosilicate, borosilicate, iron silicate, gallium silicate, chromium silicate, arsenic silicate, antimony silicate and bismuth silicate zeolites or their mixtures, and also aluminogermanate, borogermanate, gallium germanate and iron germanate zeolites or their mixtures.

Supports used for the catalysts employed in the process of the invention are preferably aluminosilicate, borosilicate and iron silicate zeolites of the pentasil type. The aluminosilicate zeolite is prepared, for example, from an aluminum compound, preferably $Al(OH)_3$ or $Al_2(SO_4)_3$ and a silicon component, preferably finely divided silicon dioxide, in aqueous amine solution, particularly in a solution of 1,6-hexanediamine, 1,3-propanediamine or triethylenetetramine, with or without addition of alkali metal or alkaline earth metal hydroxide, at 100° to 220° C. under autogenous pressure. Such a process is described in EP 0 007 081 and EP 0 007 098. Also included are the isotactic zeolites as described in EP 0 034 727 and EP 0 046 504. Depending on the amounts of starting material selected, the $SiO_2/Al_2O_3$ ratio in the aluminosilicate zeolites synthesized is 10–40,000:1 (in mol). According to another method, aluminosilicate zeolites are obtained by reaction of aluminum and silicon components in an ether such as diethylene glycol dimethyl ether, in an alcohol such as methanol or 1,4-butanediol or in water.

Borosilicate zeolites can be synthesized from a boron compound, e.g. $H_3BO_3$, and a silicon compound, preferably finely divided silicon dioxide, in the aqueous solution of an amine, particularly, 1,6-hexanediamine, 1,3-propanediamine or triethylenetetramine with or without addition of alkali metal or alkaline earth metal hydroxide, at 90° to 200° C. under autogenous pressure. In place of an aqueous amine solution, the reaction can be carried out in an ether, e.g. in diethylene glycol dimethyl ether, or in an alcohol, e.g. in 1,6-hexanediol, as solvent (cf. EP 0 007 081 and EP 0 007 098).

The iron silicate zeolites are obtained by starting from, for example, an iron compound, preferably $Fe_2(SO_4)_3$, and a silicon compound, preferably finely divided silicon dioxide, and reacting these in an aqueous solution of an amine, preferably 1,6-hexanediamine, with or without addition of alkali metal or alkaline earth meal hydroxide, at 100° to 200° C. under autogenous pressure (cf. 0 007 081 and EP 0 007 098).

After being prepared and isolated, the aluminosilicate, borosilicate or iron silicate zeolites are dried at 100° to 160° C., preferably 110° to 130° C., and then calcined at from 450° to 550°, preferably 480° to 520° C. Subsequently, they are shaped with addition of a binder, for example to form extrudates or pellets. Suitable binders are the various aluminum oxides, preferably boehmite, amorphous aluminosilicates having an $SiO_2/Al_2O_3$ weight ratio of 0.3:1 to 18:1, preferably 3:1 to 5:1, silicon dioxide, in particular finely divided $SiO_2$, mixtures of finely divided $SiO_2$ and finely divided $Al_2O_3$, finely divided $TiO_2$ and also clay. Binder and zeolite are used in a weight ratio of 90:10 to 40:60. After shaping, the shaped bodies are again dried for 10 to 20 hours at 110° to 130° C. and calcined at 400° to 550° C. for 10 to 20 hours.

Instead of calcining the zeolites immediately after preparation, isolation and drying, they can also be dried and shaped and subsequently calcined. Finally, it is also possible to omit the use of binders and to carry out the shaping process using shaping or peptizing aids such as ethylcellulose, stearic acid, potato starch, formic acid, oxalic acid, acetic acid, nitric acid, ammonia, amines, oxalic acid, acetic acid, nitric acid, ammonia, amines, silicoesters or graphite or mixtures thereof.

Zeolites which, because of the way in which they are prepared, contain alkali metal or alkaline earth metal ions but no or not enough H+ ions have to be converted into the acid, catalytically active H form by ion exchange. For this purpose, they are treated with acids or ammonium ions are introduced and they are subsequently calcined. The acidity required for the specific application can be set by means of partial ion exchange.

Furthermore, the zeolites can be modified by ion exchange or by impregnation with certain metals, for example to improve the selectivity of the reaction or to increase the catalytic life. Doping the zeolites with transition metals of groups VIB, VIIIB, IB and IIB e.g. chromium, molybdenum, tungsten, iron, nickel, copper and zinc, with noble metals such as palladium and platinum and with metals of the rare earths, e.g. lanthanum, cerium and praseodymium, has been found to be useful.

For doping by ion exchange, the shaped or unshaped zeolite is treated, for example, at temperatures of from 20° to 100° C. with an aqueous or ammoniacal solution of a salt, for example a halide, nitrate or acetate, of the above-described metals. The ion exchange can be carried out using zeolites in the hydrogen, ammonium or alkali metal form.

For example, extrudates or pellets of the zeolite in the H form are placed in a column and an ammoniacal $Pd(NO_3)_2$ solution is circulated over the shaped base at temperatures of from 30° to 80° C. for 15 to 20 hours. The zeolite is subsequently washed with water, dried at about 150° C. and calcined at about 550° C.

In another variant of the ion exchange process, pulverulent zeolite is suspended in a metal salt solution, e.g. in an ammoniacal $Pd(NO_3)_2$ solution and is stirred for about 24 hours at 40° to 100° C. After being filtered off, dried at about 150° C. and calcined at about 500° C., the modified zeolite can be further processed with or without binder to give extrudates, pellets or fluidizable material.

The doping of the zeolites by impregnation can also be carried out using metal salts, e.g. chlorides, nitrates or acetates, in aqueous, ammoniacal or alcoholic solution. One possible embodiment comprises substantially dissolving, for example, tungstic acid, $H_2WO_4$, in water and impregnating the shaped or unshaped zeolite with this solution for a particular period of time, for example 30 minutes. The water is then removed from the supernatant solution by evaporation, the zeolite is dried at about 150° C. and calcined at about 550° C. This impregnation process can be repeated a number of times until the desired metal content has been obtained.

The doping of the zeolites with metals, regardless of whether it has been carried out by ion exchange or by impregnation, can be followed by an after-treatment with hydrogen.

A further modification of the zeolites can comprise treatment with inorganic or organic acids such as hydrochloric acid, hydrofluoric acid or phosphoric acid and/or with water vapor.

As supports for catalysts which are used in the process of the invention, phosphates have also been found to be useful. Particularly suitable phosphates are aluminum phosphates, cerium phosphates, zirconium phosphates, boron phosphates, iron phosphates, strontium phosphates, silicon aluminum phosphates, silicon iron aluminum phosphates and mixtures thereof.

Supports based on aluminum phosphates for catalysts employed in the novel process are advantageously obtained by synthesis under hydrothermal conditions. These aluminum phosphates include, for example, APO-5, APO-9, APO-11, APO-12, APO-14, APO-21, APO-25, APO-31 and APO-33. These aluminum phosphates have a zeolite structure (on this subject, see Flanigen et al, Structural Synthetic and Physicochemical Concepts in Aluminophosphate-based Molecular Sieves, Innovation in Zeolite Materials Science |Editors: P. J. Grobet et al| Elsevier, 1988, p. 13 ff).

$AlPO_4$-5 (APO-5) is obtained, for example, by reacting a homogeneous mixture of orthophosphoric acid and pseudoboehmite in water, admixed with tetrapropylammonium hydroxide in an autoclave at about 150° C. for a reaction time of from 20 to 60 hours under autogenous pressure. The $AlPO_4$ filtered off is dried at 100° to 160° C. and calcined at 450° to 550° C.

$AlPO_4$ (APO-9) is synthesized from orthophosphoric acid and pseudoboehmite in an aqueous 1,4-diazabicyclo[2.2.2]-octane solution at about 200° C. under autogenous pressure, with the reaction time being 200 to 400 hours.

The synthesis of $AlPO_4$-21 (APO-21) is carried out from orthophosphoric acid and pseudoboehmite in aqueous pyrrolidine solution at 150° to 200° C. under autogenous pressure, with the reaction time being 50 to 200 hours.

Aluminum phosphates suitable as supports can also be obtained by precipitation. They are obtained, for example, by adding a solution of 268 g of $Al(NO_3)_3 \cdot H_2O$ in 780 ml of water dropwise to a solution of 92 g of diammonium hydrogen phosphate in 700 ml of water over a period of 2 hours. A pH of 8 is maintained by simultaneous addition of 25% strength $NH_3$ solution. The resulting precipitate is stirred for a further 12 hours, filtered off with suction, washed and dried at 60° C. for 16 hours.

Examples of silicon aluminum phosphates as supports for catalysts used according to the invention are SAPO-5, SAPO-11, SAPO-31 and SAPO-34. These silicon aluminum phosphates also have a zeolite structure (on this subject, see Szostak et al, Catalysis Letters 2 (1989), p. 63 ff). They are obtained by reacting a mixture of a silicon component, an aluminum component and a phosphorus component in aqueous, organic amine solutions at 100° to 250° C. under autogenous pressure for a reaction time of 2 hours to 2 weeks. SAPO-5 is obtained, for example, by mixing a suspension of $SiO_2$ in an aqueous tetrapropylammonium hydroxide solution with a suspension of pseudoboehmite and orthophosphoric acid in water and subsequently reacting this mixture at 150° to 200° C. under autogenous pressure in a stirring autoclave for a reaction time of 20 to 200 hours. The powder filtered off is dried at 110° to 170° C. and calcined at 450° to 550° C.

Other suitable silicon aluminum phosphates are, for example, ZYT-5, ZYT-6, ZYT-7, ZYT-9, ZYT-11 and ZYT-12.

Boron phosphates which can serve as supports for the catalysts used in the process are obtained, for example, by mixing and kneading concentrated boric acid and phosphoric acid, drying the mixture and calcining in an atmosphere of inert gas, air or steam at 250° to 650° C., preferably 300° to 500° C.

The supports based on phosphate can also be modified to increase the selectivity, the conversion and the life. One way of doing this is doping the unshaped or shaped phosphates with metal salts by ion exchange or impregnation. Doping is carried out using transition metals of groups IVB to VIIIB of the Periodic Table, for example titanium, zirconium vanadium, niobium, chromium, molybdenum, tungsten, manganese, rhenium, iron, ruthenium, osmium, cobalt, rhodium, iridium, nickel, palladium and platinum, transition metals of groups IB and IIB of the Periodic Table, for example copper, silver and zinc, also tin, the metals of the rare earths, for example lanthanum, cerium, praseodymium, neodymium, erbium and ytterbium, and also uranium.

Alkali metals such as lithium, potassium and caesium, alkaline earth metals such as magnesium, calcium and strontium, metals of groups IIIA, IVA and VA of the Periodic Table, for example aluminum, gallium, germanium, tin, lead and bismuth can already be present in the support material as additional promoters or can be introduced. Like the zeolites, the phosphates too can be modified by treatment with inorganic or organic acids.

Finally, metal oxides having acidic or amphoteric properties can also be employed as supports for catalysts for the reductive amination of 1,3-dioxanes. Suitable metal oxides are, for example, the acidic oxides of metals of groups IIIA and IVA and groups IVB to VIB of the Periodic Table, particularly silicon dioxide in the form of silica gel and kieselguhr, also titanium oxide, zirconium dioxide, the phosphorus oxides, vanadium pentoxide, niobium oxide, boron trioxide, aluminum oxide, molybdenum oxides, tungsten oxides and also iron oxides, either alone or as a mixture of two or more of these compounds.

It has been found to be advantageous to treat the oxides mentioned with inorganic or organic acids. Suitable inorganic acids are, for example, HF, HCl, HBr, HI, $H_2SO_4$, $H_2SO_3$, $HNO_3$, $H_3BO_3$, the phosphorus acids and their mixtures. Organic acids which are suitable for treating the oxides are, for example, formic acid, acetic acid, propionic acid and oxalic acid, alone or in admixture. Mixtures of inorganic and organic acids can also be used. The acids are allowed to act on the shaped or unshaped material.

$SiO_2$ (silica) in powder form is, for example, treated with 1 N acid for 1 hour at 80° C. and is then washed with water, dried for 16 hours at 110° C. and calcined for 20 hours at 500° C. An alternative method is to treat $SiO_2$, before or after shaping, for 1 to 3 hours at 60° to 80° C. with 3–25% strength by weight, in particular 12–20% by weight, aqueous hydrochloric acid, subsequently wash the $SiO_2$ with water, dry it and calcine it at 400° to 500° C.

According to a particularly advantageous embodiment, $SiO_2$ is treated before shaping by heating with 0.001–2 N, preferably 0.05–0.5 N, hydrofluoric acid, for example, under reflux generally for a period of 0.5 to 5 hours, preferably 1 to 3 hours. The support material is isolated, washed, advantageously dried at temperatures of 100° to 160° C. and calcined at 450° to 600° C., According to another preferred embodiment of the acid treatment, 12–20% strength by weight hydrochloric acid is allowed to act for 0.5 to 5 hours, preferably 1 to 3 hours, on $SiO_2$ after shaping at elevated temperature, e.g. 50° to 90° C., preferably 60° to 80° C. The material is subsequently washed, dried at 100° to 160° C. and calcined at 450° to 600° C. The treatment with hydrofluoric acid can also be followed by a treatment with hydrochloric acid.

Phosphoric acid is applied to the metal oxide support material, e.g. $SiO_2$, $Al_2O_3$ or $TiO_2$, by impregnation or spraying. Thus, a support containing phosphoric acid is obtained, for example, by treating $SiO_2$ with $H_3PO_4$ or $NaH_2PO_4$ solution and subsequently drying or calcining it. Phosphoric acid can also be sprayed together with silica gel in a spraying tower. This procedure is followed by drying and usually calcination. Finally, phosphoric acid can be sprayed onto silicon dioxide in an impregnation mill.

The above-described support materials of the zeolite, phosphate and metal oxide types are the basis for the catalysts used in the process of the invention. For this purpose, the supports have to be loaded with the hydrogenation-active component(s). As already mentioned, the hydrogenation-active components are metals of groups VIB, VIIIB, IB and IIB of the Periodic Table of the Elements.

The combining of support and hydrogenation-active metal can be carried out in various ways. If the supports are capable of ion exchange, then they are treated with solutions of the hydrogenation-active metals and the exchangeable cations in the crystal structure are replaced by the ions of the catalytically active metals. It is advantageous to use metal compounds whose anions are thermally unstable and can be removed by heating, for example acetate, nitrate, carbonate and oxalate. The extent of the ion exchange is determined by the ion exchange isotherms. The loading of the support with the active metal can also be combined with the doping as described above by carrying out the ion exchange using solutions which contain ions of both the hydrogenating metal and the doping metal.

In practice, the ion exchange is carried out by stirring pulverulent molecular sieves with an ammoniacal metal salt solution for 1 to 48 hours, preferably 6 to 36 hours, at 20° to 80° C. The metal concentration on the support is obtained from the difference in the metal ion concentrations before and after ion exchange. The powder loaded with the metal is washed with distilled water, dried at 110° to 160° C. and calcined at 400° to 650° C. while maintaining a heating rate of 0.1° to 10° C. $min^{-1}$.

Another method of applying the hydrogenation component comprises impregnating the catalyst support with the metal salt solution. In practice, the catalyst support, for example, is stirred with an ammoniacal solution of the metal salt at 20° to 80° C. for 1 to 48 hours, preferably 6 to 36 hours. The solvent is distilled off, the loaded support is dried at 100° to 160° C. and calcined at 400° to 650° C. In the case of the impregnation method too, application of the hydrogenation-active component and doping of the support can be carried out in one step.

A further variant for preparing hydrogenation catalysts which are suitable for the novel process is joint precipitation of hydrogenation and support components. For this, two possibilities have to be distinguished. Either the hydrogenation-active component is precipitated onto the previously made support or hydrogenation-active component and support are precipitated jointly. In practice, for example, the metal salt solution in which the support material is suspended is initially charged and the metal is precipitated as a sparingly soluble compound, for example as hydroxide, bicarbonate, carbonate or basic carbonates, onto the support using a basic reagent. In the simultaneous precipitation of hydrogenation and support components, a joint solution of the starting compounds is reacted with the precipitant. The precipitate is stirred further, optionally at room temperature or elevated temperature, filtered, washed, dried an d calcined.

Depending on the method employed, the support material is loaded with different amounts of the hydrogenation-active component. When catalysts are obtained by ion exchange, the maximum metal concentration is limited by the exchange capacity of the support material. Such catalysts usually contain 0.5 to 15% by weight of the hydrogenation-active component, based on the catalyst.

In impregnation processes, the degree of loading of the support can be varied over a wide range by varying the concentration of the metal salt solution and by repeating the impregnation procedure one or more times. Metal concentrations of 0.1 to 30, preferably 0.5 to 10 and more preferably 1 to 5, % by weight, based on the catalyst, can be obtained.

The greatest flexibility with regard to setting the metal content in the catalyst is achieved by use of precipitation processes, regardless of whether the metal component is applied to the previously made support or metal component and support component are precipitated jointly. In this procedure, the desired metal content can be determined freely by selection of the ratios of metal and support. Precipitated catalysts usually contain, depending on the metal selected, 0.1 to 30, preferably 0.5 to 10 and more preferably 1 to 5, % by weight of hydrogenation-active metal, based on the catalyst.

Pulverulent catalysts can, after isolation, drying and calcination, be shaped together with a binder to form extrudates or pellets. Suitable binders are the various aluminum oxides, preferably boehmite, amorphous alumino-silicates having an $SiO_2/Al_2O_3$ weight ratio of 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$ and clay. After shaping, the extrudates or compacts are again dried and, if desired, subsequently calcined.

Instead of providing the pulverulent catalysts with a binder, they can also be shaped immediately after drying to form pellets or extrudates and then calcined. It has been found useful to add extrusion or peptization aids to the catalyst powder, for example methylcellulose, ethylcellulose, stearic acid, potato starch, formic acid, acetic acid, oxalic acid, alkali metal hydroxide solution, ammonia, amines or graphite.

Extrudate and tablet sizes depend on the individual requirements. The catalysts are usually used as extrudates of 2 to 4 mm, as tablets having a diameter of 3 to 5 mm, as pellets having a size of 1.0 to 1.6 mm or in powder form, for example also as fluidizable material having particle sizes between 50 and 400 µm.

The process of the invention can be carried out batchwise or continuously. The batchwise reaction procedure is carried out in autoclaves or pressure tubes. Continuous operation can be carried out in fixed-bed or moving-bed reactors. Fixed-bed reactors are, for example, loop reactors, tray reactors, circulating gas reactors and preferably tube reactors. In the case of tube reactors, the ratio of reactor diameter to catalyst pellet size is advantageously 2:1 to 20:1 and particularly 4:1 to 10:1.

In the following examples, there are described several preferred embodiments to illustrate the invention. However, it is to be understood that the invention is not intended to be limited to the specific embodiments.

Catalyst A

The catalyst comprised 5% by weight of copper (based on the catalyst in the unreduced state) as hydrogenation-active metal and boron zeolite of the pentasil type as support. The boron zeolite was prepared by hydrothermal synthesis. For this purpose, 640 g of finely divided $SiO_2$ and 122 g of $H_3BO_3$ were allowed to react with one another in the presence of 8.000 g of an aqueous 1,6-hexanediamine solution (hexanediamine:water=1:1 in parts by weight) at 170° C. under autogenous pressure in a stirring autoclave. The crystalline reaction product was filtered off, washed, dried for 24 hours at 100° C. and calcined for 24 hours at 500° C. The zeolite had the composition 94.2% by weight of $SiO_2$ and 2.3% by weight of $B_2O_3$. The pulverulent material was formed into extrudates with addition of an extrusion aid, and the extrudates were dried for 16 hours at 110° C. and calcined for 24 hours to 500° C.

The loading of the support material with the hydrogenation-active metal was carried out by impregnation with an aqueous $Cu(NO_3)_2.3H_2O$ or $Cu(CH_3COO)_2.H_2O$ solution whose copper content corresponded to the desired copper content of the catalyst, being pumped at 70° to 80° C. for 24 hours over the support. The treatment time could be significantly shortened by addition of ammonia (as 25% strenght aqueous solution) to the metal salt solution until a pH of about 10.5 was reached. The metal loading was complete when the intense blue color of the ammoniacal copper salt solution had disappeared.

The impregnated support was washed with distilled water, dried for 12 hours at 160° C. and calcined for 5 hours at 550° C.

Catalyst B

Catalyst B was a product of Südchemie, Munich, which is sold under the designation G69 in pellet form. In comprised about 50% by weight of Ni and about 2.4% by weight of $ZrO_2$ on kieselguhr.

Catalyst C

Catalyst C comprised as support a zeolite of the type H-BEA from PQ Corporation (sold under the product designation Valfor CP-806B) having a molar $SiO_2/Al_2O_3$ ratio of 25. The support was impregnated with a copper salt solution and the copper content of the catalyst was 5% by weight and its surface area was 750 m²/g.

Catalyst D

Catalyst D comprised as support a zeolite of the US-Y type, a commercial product of PQ Corporation (product designation: CBV 600) having a molar $SiO_2/Al_2O_3$ ratio of 5.2. The support was impregnated with a nickel nitrate solution and the nickel content of the catalyst was 10% by weight and its surface area was 660 m²/g.

Catalyst E

Catalyst E comprised as support a zeolite of the US-Y type, a commercial product of PQ Corporation (product designation: CBV 600) having a molar $SiO_2/Al_2O_3$ ratio of 5.2 The support was impregnated with a nickel nitrate solution and the nickel content of the catalyst was 15% by weight and its surface area was 600 m²/g.

EXAMPLES 1 to 16

The reactions were carried out under isothermal conditions in a coiled tube reactor (diameter: 8 mm; length: 1,000 mm) for reaction times of 1 to 8 hours. In the tube reactor, there was located, over the catalyst bed, a pre-vaporizer section to heat the starting materials to reaction temperature. The reaction mixture was condensed in a cold trap at −33° C., warmed to room temperature and analyzed by gas chromatography. The test conditions and the test results are summarized in the following table.

TABLE

| | | | | | | | | |
|---|---|---|---|---|---|---|---|---|
| Reductive amination of 5,5-dimethyl-2-phenyl-1,3-dioxane (dissolved in 1,3-dioxane in a molar ratio of 1:4) | | | | | | | | |
| Example | Catalyst | T [°C.] | P [MPa] | Dioxane/NH$_3$/H$_2$ [mol/mol/mol] | Throughput [g g$^{-1}$h$^{-1}$] | dioxane conversion [%] | Selectivity in respect of amine [%] | Test duration [h] |
| 1 | A | 350 | 0.1 | 1:6:45 | 1 | 81 | 25 | 1 |
| 2 | A | 350 | 0.1 | 1:6:45 | 1 | 42 | 7 | 6 |
| 3 | A | 300 | 0.1 | 1:6:45 | 1 | 19 | 18 | 6 |
| 4 | B | 300 | 0.1 | 1:4:30 | 1 | 41 | 27 | 6 |
| 5 | B | 300 | 0.1 | 1:13:100 | 0.3 | 81 | 9 | 6 |
| 6 | B | 300 | 0.1 | 1:4:1 | 1 | 31 | 23 | 8 |
| 7 | B | 300 | 0.1 | 1:4:3 | 1 | 42 | 19 | 8 |
| 8 | B | 300 | 0.1 | 1:2:30 | 1 | 39 | 31 | 8 |
| 9 | B | 300 | 0.1 | 1:8:30 | 1 | 36 | 23 | 8 |
| 10 | B | 325 | 0.1 | 1:4:30 | 1 | 57 | 27 | 8 |
| 11 | B | 275 | 0.1 | 1:4:30 | 1 | 33 | 15 | 8 |
| 12 | C | 300 | 0.1 | 1:4:30 | 1 | 91.8 | 10.5 | 4 |
| 13 | D | 300 | 0.1 | 1:4:30 | 1 | 91.9 | 17.8 | 4 |
| 14 | E | 300 | 0.1 | 1:4:30 | 1 | 88.1 | 13.5 | 7 |
| 15 | E | 300 | 0.1 | 1:4:6 | 1 | 76.7 | 15.9 | 7 |
| 16 | E | 325 | 0.1 | 1:4:6 | 1 | 90.8 | 31.2 | 7 |

Various modifications of the process of the invention may be made without departing from the spirit or scope thereof and it should be understood that the invention is intended to be limited only as defined in the appended claims.

What we claim is:

1. A process for preparing 4-oxa-amines of the formula of the formula

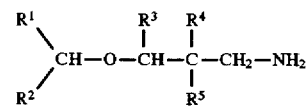

wherein $R^1$, $R^2$, $R^4$ and $R^5$ are individually selected from the group consisting of a) hydrogen, b) alkyl, alkenyl and alkynyl up to 18 carbon atoms, c) cycloalkyl and cycloalkenyl of 5 to 8 carbon atoms, d) aryl, alkylaryl, aralkyl, aralkenyl and alkenylaryl of 6 to 16 carbon atoms and e) heterocyclics or $R^1$ and $R^2$ and/or $R^4$ and $R^5$ together with the carbon atom to which they are bound can form a cycloalkane, cycloalkene or a heterocycle, $R^1$, $R^2$, $R^4$ and $R^5$ optionally have substituents which are inert under the reaction conditions, and $R^3$ is hydrogen or alkyl comprising reacting 1,3-dioxanes of the formula

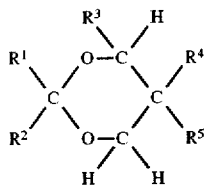

wherein $R^1$, $R^2$, $R^3$, $R^4$ and $R^5$ are as defined above, with hydrogen and ammonia at pressures of 0.1 to 35 MPa and temperatures of 40° to 500° C. in the presence of a hydrogenation catalyst.

2. The process of claim 1, wherein the 1,3-dioxanes are compounds of the formula

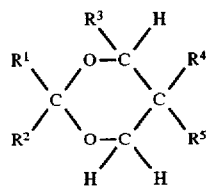

wherein $R^1$, $R^2$, $R^4$ and $R^5$ are individually selected from the group consisting of hydrogen, alkyl of 1 to 12, alkenyl and alkynyl of 2 to 12 carbon atoms, cycloalkyl or cycloalkenyl of 5 to 6 carbon atoms, aryl, alkylaryl, aralkyl, aralkenyl or alkenylaryl of 6 to 12 carbon atoms and heterocyclics containing at least one ring member selected from the group consisting of nitrogen, oxygen and sulfur, and $R^3$ is alkyl of 1 to 12 carbon atoms.

3. The process of claim 1 wherein $R^3$ is hydrogen.

4. The process of claim 1, wherein the hydrogenation catalysts are supported catalysts.

5. The process of claim 4, wherein the hydrogenation catalysts comprise zeolites as supports.

6. The process of claim 5, wherein the support is a zeolite of the pentasil type.

7. The process of claim 6, wherein the zeolite is an aluminosilicate, borosilicate or iron silicate zeolite of the pentasil type.

8. The process of claim 6, wherein the zeolite is doped with transition metals selected from the group consisting of groups VIB, VIIIB, IB, and IIB of the Periodic Table.

9. The process of claim 6, wherein the zeolite is doped with noble metals.

10. The process of claim 6, wherein the zeolite is doped with metals of the rare earths.

11. The process of claim 1, wherein the hydrogenation catalyst comprises phosphates as support.

12. The process of claim 1, wherein the hydrogenation catalyst is selected from the group consisting of aluminum phosphate, cerium phosphate, zirconium phosphate, boron phosphate, iron phosphate, strontium phosphate, silicon aluminum phosphate, silicon iron aluminum phosphate, and a mixture of two or more of the phosphates, as support.

13. The process of claim 11, wherein the phosphates are a member of the group consisting of doped transition metals of groups IVB to VIIIB, IB or IIB and metals of the rare earths.

14. The process of claim 1, wherein the hydrogenation catalyst comprises a metal oxide as support.

15. The process of claim 14, wherein the support is an oxide of a metal selected from the group consisting of groups IIIA, IVA or groups IVB to VIB of the Periodic Table and mixtures of two or more such oxides.

16. The process of claim 5, wherein the zeolites, phosphates and/or metal oxides are treated with inorganic or organic acids.

17. The process of claim 1, wherein the hydrogenation catalysts comprise as hydrogenation-active components a metal or a plurality of metals selected from the group consisting of VIB, VIIIB, IB and IIB of the Periodic Table.

18. The process of claim 17, wherein the hydrogenation-active component is selected from the group consisting of molybdenum, tungsten, ruthenium, iron, osmium, cobalt, rhodium, iridium, nickel, palladium, platinum, copper, silver or zinc.

19. The process of claim 1, wherein the reaction is carried out at pressures of from 3 to 15 MPa and at temperatures of from 100° to 450° C.

20. The process of claim 1, wherein the molar ratio of ammonia to the 1,3-dioxane is from 0.2:1 to 100:1.

21. The process of claim 1, wherein the molar ratio of hydrogen to 1,3-dioxane is from 0.2:1 to 250:1.

* * * * *